United States Patent
Maiz-Aguinaga et al.

(10) Patent No.: US 10,321,858 B2
(45) Date of Patent: Jun. 18, 2019

(54) APPARATUS AND METHODS FOR TRANSDERMAL SENSING OF ANALYTES IN INTERSTITIAL FLUID AND ASSOCIATED DATA TRANSMISSION SYSTEMS

(71) Applicant: ProteaDX, Inc., Palo Alto, CA (US)

(72) Inventors: Jose Antonio Maiz-Aguinaga, Vancouver, WA (US); Lennart Olsson, Los Altos Hills, CA (US)

(73) Assignee: ProteaDX, Inc., Palo Alto, CA (US)

(*) Notice: Subject to any disclaimer, the term of this patent is extended or adjusted under 35 U.S.C. 154(b) by 339 days.

(21) Appl. No.: 14/827,186

(22) Filed: Aug. 14, 2015

(65) Prior Publication Data

US 2016/0058342 A1  Mar. 3, 2016

Related U.S. Application Data (60) Provisional application No. 62/070,182, filed on Aug. 18, 2014.

(51) Int. Cl.
*A61B 5/145* (2006.01)
*A61B 5/1473* (2006.01)
*A61B 5/00* (2006.01)

(52) U.S. Cl.
CPC .......... *A61B 5/14514* (2013.01); *A61B 5/685* (2013.01); *A61B 5/0004* (2013.01); *A61B 5/1473* (2013.01); *A61B 5/14532* (2013.01); *A61B 5/14539* (2013.01); *A61B 5/14546* (2013.01); *A61B 5/4845* (2013.01); *A61B 2505/07* (2013.01)

(58) Field of Classification Search
CPC .................................................. A61B 5/14514
See application file for complete search history.

(56) References Cited

U.S. PATENT DOCUMENTS

| | | | |
|---|---|---|---|
| 6,471,903 B2 | 10/2002 | Sherman | |
| 6,591,124 B2 | 7/2003 | Sherman | |
| 6,908,453 B2 | 6/2005 | Fleming | |
| 7,132,054 B1 | 11/2006 | Kravitz | |
| 7,344,499 B1* | 3/2008 | Prausnitz | A61M 37/0015 600/309 |
| 7,416,541 B2 | 8/2008 | Yuzhakov | |
| 7,473,244 B2 | 1/2009 | Frazier | |
| 7,941,201 B2 | 5/2011 | Chiou | |
| 8,303,518 B2 | 12/2012 | Aceti | |
| 8,560,059 B2 | 10/2013 | Hoarau | |
| 8,920,359 B2 | 12/2014 | Kodgule | |
| 2002/0193754 A1* | 12/2002 | Cho | A61M 37/0015 604/272 |

(Continued)

FOREIGN PATENT DOCUMENTS

| | | |
|---|---|---|
| EP | 1 418 977 B1 | 1/2007 |
| EP | 1 439 871 B1 | 1/2009 |

(Continued)

*Primary Examiner* — Daniel J Colilla
(74) *Attorney, Agent, or Firm* — David L. Fitzgerald (57) ABSTRACT

Provided are transdermal microneedle-based devices for sensing the presence and concentration of analytes such as electrolytes, biomarkers, drugs, and proteins in interstitial fluid. Also provided are methods and systems to transmit the data obtained by wired or wireless connection to a receiver and to relay the data to the user or a clinician.

20 Claims, 7 Drawing Sheets

(56) References Cited

U.S. PATENT DOCUMENTS

| | | | |
|---|---|---|---|
| 2005/0100937 A1* | 5/2005 | Holmes | A61B 5/0024 435/6.12 |
| 2006/0019327 A1* | 1/2006 | Brister | A61B 5/0002 435/25 |
| 2006/0094944 A1* | 5/2006 | Chuang | A61B 5/14514 600/347 |
| 2007/0239068 A1* | 10/2007 | Rasch-Menges | A61B 5/14514 600/573 |
| 2008/0312518 A1* | 12/2008 | Jina | A61B 5/0002 600/345 |
| 2009/0062752 A1 | 3/2009 | Gonnelli | |
| 2009/0099427 A1 | 4/2009 | Jina | |
| 2010/0025238 A1 | 2/2010 | Gottlieb | |
| 2011/0105871 A1 | 5/2011 | Zimmermann | |
| 2011/0319920 A1* | 12/2011 | Kikkawa | A61B 5/1411 606/186 |
| 2012/0172692 A1* | 7/2012 | Tamada | A61B 5/14514 600/365 |
| 2012/0186997 A1 | 7/2012 | Li | |
| 2012/0190950 A1 | 7/2012 | Yang | |
| 2014/0287942 A1* | 9/2014 | Mahmood | C12Q 1/6837 506/9 |
| 2014/0336487 A1 | 11/2014 | Wang | |
| 2017/0127984 A1* | 5/2017 | Pushpala | A61B 5/14514 |

FOREIGN PATENT DOCUMENTS

| | | |
|---|---|---|
| EP | 1 448 263 B1 | 1/2009 |
| EP | 1 841 491 B1 | 5/2009 |
| WO | WO 01/ 049346 A2 | 7/2001 |
| WO | WO 2014/ 120114 A2 | 8/2014 |

\* cited by examiner

Server/ cloud

APPARATUS AND METHODS FOR TRANSDERMAL SENSING OF ANALYTES IN INTERSTITIAL FLUID AND ASSOCIATED DATA TRANSMISSION SYSTEMS

CROSS-REFERENCE TO RELATED APPLICATIONS

This application claims priority under 35 U.S.C. § 119 (e) from U.S. Provisional Application Ser. No. 62/070,182 filed 18 Aug. 2014.

BACKGROUND OF THE INVENTION

The present invention relates to biomedical testing of body fluids, to sensing device processing and fabrication, and more particularly to a method of fabricating a transdermal or interstitial fluid analyzer that integrates microneedles with micro-sensors with multiple integration layers and structures. The analyzer uses a specially fabricated applicator, patch, or carrier to communicate with a smart device, analyze the sensed data, and communicate the results to both patient and medical personnel.

Frequent testing for biological materials such as $K^+$, $Na^+$, $Cl^-$ ions, glucose, creatinine, cholesterol as well as therapeutic agents such as drugs used in the treatment of cardiovascular, renal, neurological, oncological, and other medical conditions is often required for the effective treatment and monitoring of patients. The standard of care involves blood extraction in a clinical setting with subsequent serum analysis for the concentrations of one or more electrolytes or other biological or therapeutic molecules of interest.

This testing process results in high costs related to performing the blood or fluid extraction in a clinical setting, delays of hours to days related to the testing frequently being done by specialized personnel or laboratories, and inconvenience to the patient related to travel to the medical facility and the significant time required. As a result, testing is often performed at suboptimal frequency and risks a delayed response to a medically significant event.

The use of microneedles that can perforate the stratum corneum (the outer layer of the epidermis) and reach the transdermal fluid under the skin is part of the existing state of the art. When made hollow, the microneedles provide access to the interstitial fluid among subcutaneous cells and permit the delivery of drugs or access to the interstitial fluid for analysis. Microneedles have been made from a large variety of materials, from metals to ceramics to polymers to silicon, with varying degrees of performance and process control. While these microneedles can access the transdermal region, when manufactured to the correct dimensions, they are not deep enough to reach the blood capillaries or nerve endings. Their application is therefore practically painless and does not produce bleeding.

Research in the use of microneedles has focused mostly on methods for delivering drugs into the subcutaneous region. Separately, sensors using specially formulated biochemical films to obtain electrical readings and transistors fabricated in semiconductors such as silicon, modified to be sensitive and specific for ions such as $K^+$ have also been occasionally described. Key difficulties with existing approaches are the lack of sufficient process control to achieve medical grade devices and complex integration methods that are not best suited for the high volume manufacturing necessary to achieve large volumes and low cost. As a result, to the best knowledge of the inventors, practical devices that allow routine testing of transdermal fluid at low cost by non-specialized personnel are not available in the marketplace.

The following patents and publications relate to the field of the invention.

| Patent | Publication date | Applicant | Title |
|---|---|---|---|
| U.S. Pat. No. 8,920,359B2 | Dec. 30, 2014 | Wockhardt Res. Centre | A device and a system for delivery of biological material |
| US20140336487 | Nov. 13, 2014 | The Regents of the Univ. of Cal. | Microneedle arrays for biosensing and drug delivery |
| 62/070,182 | Provisional Aug. 18, 2014 | Jose Maiz | Apparatus' and methods for transdermal and interstitial body fluid examination, sensing and associated data transmission systems |
| WO2014120114 | Aug. 7, 2014 | Empire Tech. development | Microneedle-based natremia sensor and methods of use |
| U.S. Pat. No. 8,560,059B2 | Oct. 5, 2013 | Covidien Hoarau | System and methods for optical sensing and drug delivery using microneedles |
| U.S. Pat. No. 6,591,124B2 | Jul. 8, 2013 | Procter & Gamble | Portable Interstitial Fluid Monitoring System |
| U.S. Pat. No. 8,303,518B2 | Nov. 6, 2012 | Intuity Medical | Autonomous, ambulatory analyte monitor or drug delivery device |
| US20120190950 | Jul. 26, 2012 | Medtronic Minimed Inc | Electrode compositions for use with analyte sensors |
| US20120186997 | 26 Jul. 2012 | Medtronic Minimed Inc | Layered enzyme compositions for use in analyte sensors" |
| U.S. Pat. No. 7,941,201 | May 10, 2011 | Nat Chiao Tung Univ | Microprobe array structure and method for manufacturing the same |
| US20110105871 | May 5, 2011 | The Regents of the Univ. of Cal. | Monitoring method and/or apparatus |
| US20100025238 | Feb. 4, 2010 | Medtronic Minimed, Inc. | Analyte sensor apparatuses having improved electrode configurations and methods for making and using them |
| EP1841491B1 | May 27, 2009 | Janisys | Transdermal drug delivery device |
| US20090099427 | Apr. 16, 2009 | Arkal Medical, Inc. | Microneedle array with diverse needle configurations |

-continued

| Patent | Publication date | Applicant | Title |
|---|---|---|---|
| US20090062752 | Mar. 5, 2009 | Gonnelli Robert R | Switchable microneedle arrays and systems and methods relating to same |
| EP1439871B1 | Jan. 14, 2009 | Massachusetts Inst Technology | Microneedle transport device |
| EP1448263B1 | Jan. 7, 2009 | Power Paper Ltd Mavor | Device and method for controlled delivery of active substance into the skin |
| U.S. Pat. No. 7,473,244B2 | Jan. 6, 2009 | Univ Utah Frazier | Active needle devices with integrated functionality |
| U.S. Pat. No. 7,416,541 | Aug. 26, 2008 | Corium International, Inc. | Intracutaneous microneedle array apparatus |
| U.S. Pat. No. 7,344,499B1 | Mar. 18, 2008 | Georgia Tech Research Corp. | Microneedle device for extraction and sensing of bodily fluids |
| EP1418977B1 | Jan. 10, 2007 | Hospira, Cho | Microneedles for minimally invasive drug delivery and method of manufacturing the same |
| U.S. Pat. No. 7,132,054B1 | Nov. 7, 2006 | Sandia Corporation | Method to fabricate hollow microneedle arrays |
| U.S. Pat. No. 6,908,453B2 | Jun. 21, 2005 | 3M Innovative Properties Co | Microneedle devices and methods of manufacture |
| U.S. Pat. No. 6,471,903B2 | Oct. 29, 2002 | The Procter & Gamble Company | Apparatus and method for manufacturing an intracutaneous microneedle array |
| WO2001049346 | Jul. 12, 2001 | Redeon Inc | Stacked microneedle systems |

BRIEF SUMMARY OF THE INVENTION

The invention provides processes and methods that enable and make practical the integration of microneedles with biochemical micro-sensors and other associated or useful elements such as reference electrodes, pH sensors, and temperature sensors. The invention further allows for their miniaturization to achieve low cost and high precision manufacturing methods required for a dependable and accurate medical grade device. It achieves these objectives by implementing innovative process and integration architectures that leverage, adapt, and take advantage of the state of the art in semiconductor wafer and thin film processing and in materials with biochemical sensor devices and membranes that have been proposed for biochemical testing. As described below, in particular implementations the invention provides a specialized applicator or carrier that allows the use of the device by non-specialized medical personnel or patients themselves. Built-in data analysis and communication capabilities allow the results to be communicated in real time to the patient and/or to medical staff (doctor, nurse, etc.) without any specialized or skilled action by the user. The overall system described by the invention achieves a low cost, medical grade, easy-to-use transdermal and interstitial sensor architecture suitable for use in both clinical and non-clinical environments by non-specialized personnel as well as by the patient him(her)self. To the best understanding of the inventors, this capability to simultaneously achieve low cost, ease of use, medical grade accuracy and suitability for high volume manufacturing has not been accomplished by integration architectures described in the prior art, and no equivalent capability devices have been offered or are in the process of being offered in the marketplace.

BRIEF DESCRIPTION OF THE DRAWINGS

The advantages of the invention can be more readily be ascertained from the following description of the invention when read in conjunction with the accompanying drawings.

DETAILED DESCRIPTION OF THE INVENTION

In the following detailed description, reference is made to the accompanying drawings that show, by way of illustration and examples, some specific embodiments in which the invention may be practiced. These embodiments are described in sufficient detail to enable those skilled in the art to practice the invention. Although the various embodiments of the invention are different, they are in no way mutually exclusive. For example, a particular feature, structure, or characteristic described in connection with one embodiment may be implemented within other embodiments without departing from the spirit and scope of the invention. In addition, it is to be understood that the location or arrangement of individual elements within each disclosed embodiment may be modified without departing from the spirit and scope of the invention. The following description is therefore not to be taken in a limiting sense, but only as a means to illustrate and explain the scope of the invention which is defined only by the appended claims, appropriately interpreted, along with the full range of equivalents to which the claims are entitled. In the drawings, like numerals refer to the same or similar functionality throughout the several views.

Methods of forming transdermal and interstitial fluid sensing and data transmission systems (i.e., the integration of microneedles, micro-sensors, reference electrodes, applicators, wireless communication and data processing capabilities) and associated structures are described. Those methods comprise forming a microneedle unit that can pierce the stratum corneum of the skin; forming a micro-sensor unit for the ion or molecule species of interest (e.g., electrolytes, biomolecules, and drugs, whether therapeutic or otherwise) along with its associated control circuitry; forming a reference electrode; integrating all of them as a self-contained consumable unit in a way that can be greatly miniaturized to reduce cost; forming an applicator, patch, holder, or carrier that holds the consumable during the test, powers the sensors, acquires the data and transmits it to a smart device. The methods of the invention provides a device that is safe and easy to use by non-specialized personnel. The invention also provides an application for the smart device specifically developed to direct the sensing event, analyze the results, and send them in real time to the patient and/or appropriate medical personnel.

Figure 1:
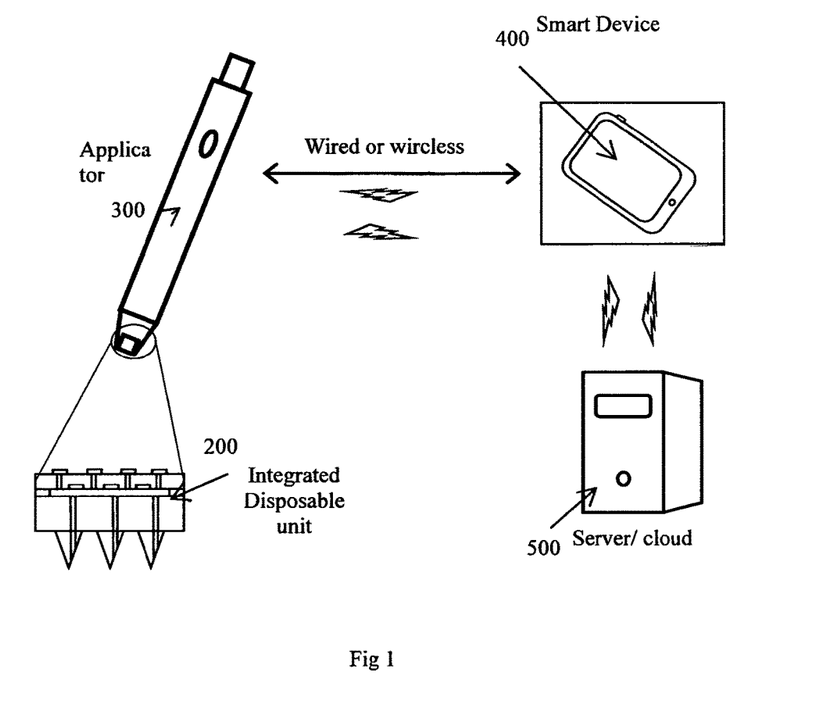
FIG. 1 represents the overall transdermal sensing apparatus consisting of the integrated microneedle/sensor element 200, a specially designed applicator 300 with a wired or wireless connection system to a smart device, an application for the smart device 400 to direct the sensing event and analyze results, a wired or wireless connection to a data server or the cloud, and a software application in the server or cloud 500 for data analysis, storage and distribution while preserving the medically required protocols for privacy and data integrity.

An embodiment of the invention, as illustrated in FIG. 1, provides an integrated system capable of transdermal and cell interstitial fluid examination and sensing of analytes, biomarkers, and drug concentrations. An integrated disposable sensing unit 200 is fabricated by forming microneedles, micro-sensors, a reference electrode, and their supporting electronic circuitry integrated into a unit that is suitable for low cost manufacturing and easy to handle by non-specialized personnel. An applicator 300 such a pen-like, patch-like, or other carrier with a different form factor but the same function is reusable and specially designed to handle the integrated disposable unit. This applicator 300 carries a battery unit to provide power, includes electronic circuits to power the sensors and read the resulting sensing data, additional electronic circuits for processing and preparing that data for transmission, along with electronic circuits to transmit the data by wireless or wired connection to a smart device. A smart device 400 such as a smartphone, smart watch, smart bracelet, or general computing device capable of sending data to and receiving data from the applicator, together with a software application directs the sensing event, analyzes the sensing results, and communicates it to a central or cloud based data repository system and/or the patient and authorized clinician or clinic. A computing device 500 interacts with a specially designed software application, whether local, at a dedicated server farm, or in the cloud, to accept the data, store it, and provide secure access to only authorized personnel using protocols generally accepted to handle sensitive medical information.

Figure 2A:
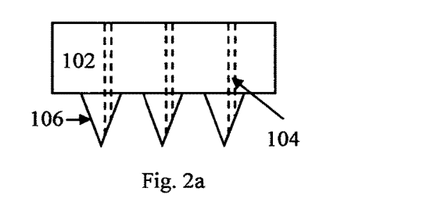
FIGS. 2a-2d represent cross-sections of structures used to form the integrated micro-sensor unit. The integrate the operation of the microneedles with the micro-sensors and a reference electrode in a monolithic block of silicon with a surrounding packaging structure that provides for a microfluidics chamber and electrical connections which may be formed when carrying out an embodiment of the method of the invention.

In an embodiment of the invention, as illustrated in FIGS. 2a-2d, a method of forming an integrated disposable sensing unit 200 involves forming microneedles, micro-sensors for one or multiple analytes or biochemical species of interest, and a reference electrode and integrating them into a unit suitable for low cost manufacturing and easy to handle by non-specialized personnel. Referring to FIG. 2a, an array of micro-needles 106 are fabricated on a silicon block 102 by using photolithographic techniques, preferential crystal plane wet etch methods, isotropic and anisotropic dry etch techniques or a combination of all of them as is well known to those skilled in the art. In this embodiment, the length of the microneedles is between 25 micrometers and several millimeters as appropriate to the specific sensing function pursued. In the case of transdermal sensing, lengths between 25 micrometers and 500 micrometers can be considered to ensure perforation of the stratum corneum and perform the testing without any significant pain or bleeding. Dimensions between 25 micrometers and several millimeters can be considered when probing for cell interstitial fluids in diseased body tissues. The microneedles and supporting silicon block are formed with hollow perforations 104 which are formed commonly but not exclusively by Deep Reactive Ion Etching (DRIE) or alternative techniques as is well known to those skilled in the art.

Figure 2B:
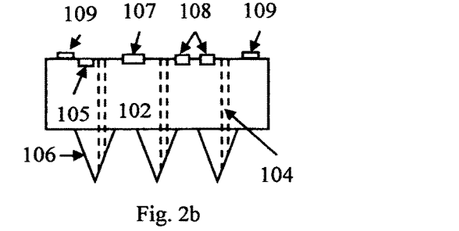

FIG. 2b illustrates the formation of micro-sensors 108 designed to measure presence or concentration of the ion or biomolecule of interest, a reference electrode 107, and electronic circuitry 105 designed to power and control them, with all of them being formed on the surface opposite from that used to form the microneedles by using photolithography and commonly used thin and thick film processing techniques. These micro-sensors 108 can be formed in a manner optimized for the specific ion species, biomarker, or drug, and could be based on Ion Sensitive Field Effect Transistors, specially modified thin films whose conductivity is modulated by the concentration of the chemical species to be tested or optimized to use voltammetry or amperometry techniques, as is known to those skilled in the art. The micro-sensors 108 could be all similar so as to measure the concentration of a single species of analyte, biomarker, or drug, or may be formed to contain multiple sensor types so that multiple types of analytes, biomarkers, and drugs can be measured simultaneously. The reference electrode 107 can be formed by adapting processing techniques commonly used in semiconductor technology and the use of different kinds of materials but preferably as a Ag/AgCl reference electrode as is commonly used by those skilled in the art. The sensors 108 may be formed to include measurements of pH, temperature, ions such as $K^+$, $Na^+$, $Cl^-$ and others, important biomolecules such as creatinine, glucose, lactic acid, lactates, cholesterol, nitrates, etc., therapeutic drugs such as those used to treat cardiovascular, renal, neurological, and oncological conditions, or any other species of biological interest. The same FIG. 2b illustrates the formation of specially designed electronic circuits 105 and metallic contacts 109 on the same surface as the micro-sensors 108 whose function is to power the micro-sensors, read the sensing results, and prepare the data for transmission to the electronic circuits in the applicator through the metallic contacts 109, which are formed by standard processing techniques used to fabricate semiconductor devices.

Figure 2C:
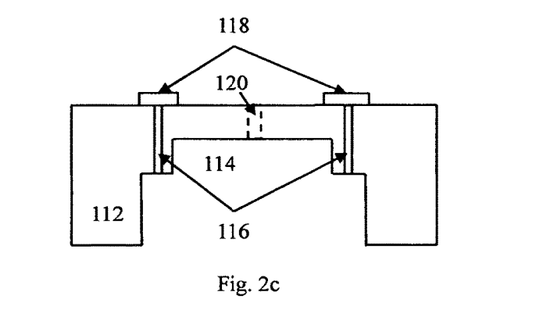
Figure 2D:
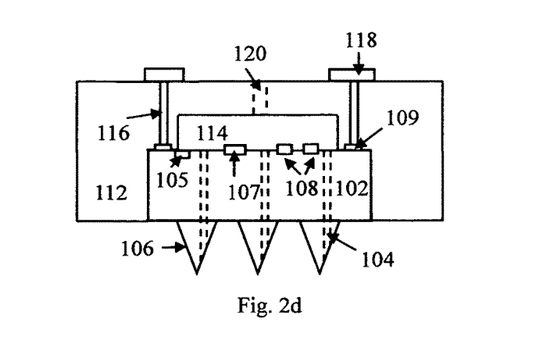

Referring to FIGS. 2c and 2d, a specially formed casing 112 is used to assemble the micro-needle/micro-sensor(s) integrated block in a way that it creates a microfluidics chamber 114 and which allows the transdermal fluid to reach the sensor units. Making the dimensions of the hollow portion of the microneedle 104 and the fluid chamber 114 small and their surfaces hydrophilic, along with the presence of a vent 120, will allow the transdermal fluid to travel by capillary action and reach the micro-sensors. Preferred embodiments for the hollow portion of the microneedles are below 150 micrometers, although larger dimensions are possible. Preferred embodiments for the height of the microfluidics chamber are in the range 10-500 micrometers although dimensions of 1 millimeter and larger can be made to work. The casing 112 may comprise materials such as metals, ceramics, polymers, plastics, or other materials that provide similar structural function. Perforations 116 in the casing 112 are used to incorporate electrical conductors and provide electrical access to the sensors 108 and sensing circuitry 105, provide power, and read the results, and may be formed in sufficient quantity to tend the needs of the multiple sensors formed. A perforation formed in the casing 112 and identified as a vent 120 allows air to be vented out of the chamber as the transdermal fluid fills the sensing chamber 114 by capillary action and can be formed anywhere that is convenient in the wall's microfluidics chamber. Conductive pads 118 are formed on the casing to complete forming the consumable unit (FIG. 2d). In a preferred embodiment the integrated disposable unit 200, described in more detail in FIG. 2d, is between 0.5 millimeters and 10 millimeters wide with the dimension being dictated primarily by number of distinct sensor devices incorporated into the unit. In a preferred embodiment the integrated disposable unit 200 has a thickness between 500 micrometers and 5 millimeters.

In another embodiment, referring to the same FIGS. 2a-2d, the substrate 102 and micro-needles 106 are formed in a material different from silicon such as metal, ceramic, polymer, carbon, or plastic, and the micro-sensors 108, controlling circuitry 105 and reference electrode 107 are fabricated separately either in silicon or in another suitable material such as a different semiconductor, carbon, metal, or nanoparticle structure, and are placed appropriately over the substrate 102 while allowing a similar method of integration of the consumable portion of the device.

Figure 3A:
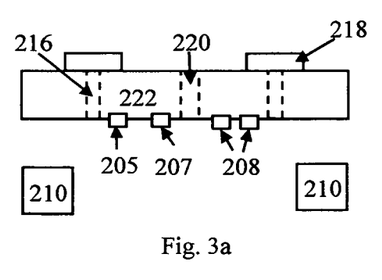
FIGS. 3a-3c represent cross-sections of structures that integrate the operation of the microneedles with the micro-sensors and reference electrode as fabricated in separate blocks of silicon, a spacer enabling the formation of a microfluidics cavity, and the surrounding packaging structure which may be formed when carrying out another embodiment of the method of the invention.
Figure 3B:
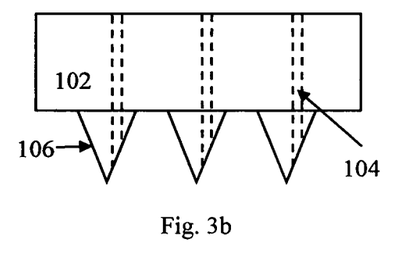
Figure 3C:
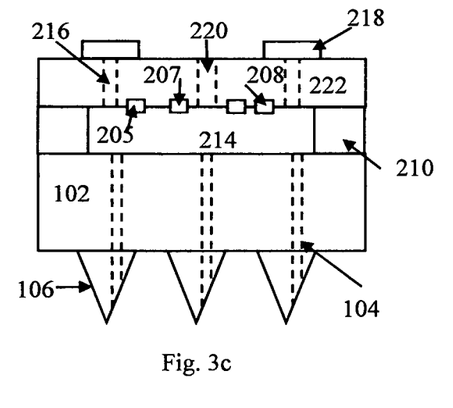

In another embodiment, as described in FIGS. 3a-3c, the substrate 102 with the microneedles 106 (FIG. 3b) is formed in a separate block from the micro-sensors 208, control circuitry 205, and reference electrode 207 which are formed on a substrate 222 as described in FIG. 3a. The microneedles 106 and the micro-needle substrate 102 can be formed in a variety of materials including, but not limited to silicon, metals, ceramics, polymers, carbon, or plastics. The substrate 222 can be formed in a variety of materials including, but not limited to silicon, metals, ceramics, polymers, carbon, or plastics. The micro-sensors themselves 208 can be formed in silicon or in another material suitable for the fabrication of micro-sensors such as a different type of semiconductor. Alternatively a properly formulated carbon or polymer based paste could be based on Ion Sensitive Field Effect Transistors, specially modified thin films whose conductivity is modulated by the concentration of the chemical species to be tested or optimized to use voltammetry or amperometry techniques, as is known to those skilled in the art. The controlling circuitry 205 and reference electrode 207 can then be formed on substrate 222. When the structure containing the sensors 208, control circuitry 205, and electrode 207 is integrated with the structure containing the microneedles 106 and microneedle substrate 102, a spacer 210 enables the formation of a microfluidics cavity 214 as shown in FIG. 3c. In this embodiment, the electrical connections 216, electrical contacting pads 218 and the vent 220 are also formed in the substrate 222. During operation, and when the transdermal needles 106 pierce the stratum corneum, the interstitial fluid moves up the hollow portion of the needle 104 by capillary action reaching the cavity 214 and the micro-sensors 208 and generates an electrical sensing signal that can be read through the electrical pads 218.

Figure 4A:
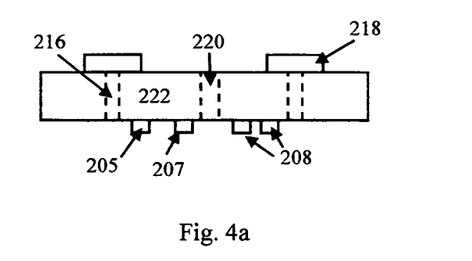
FIGS. 4a-4c represent cross-sections of structures that integrate the operation of the microneedles with the sensors and reference electrode as fabricated in separate blocks of silicon but where the etching in one of the silicon-forming blocks provides for the microfluidics chamber, as may be formed when carrying out yet another embodiment of the method of the invention.
Figure 4B:
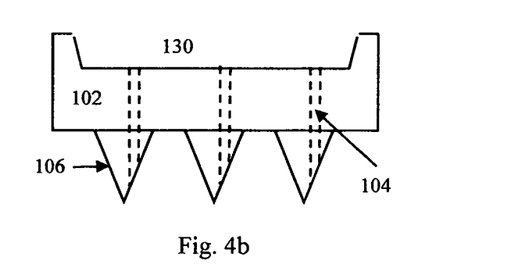
Figure 4C:
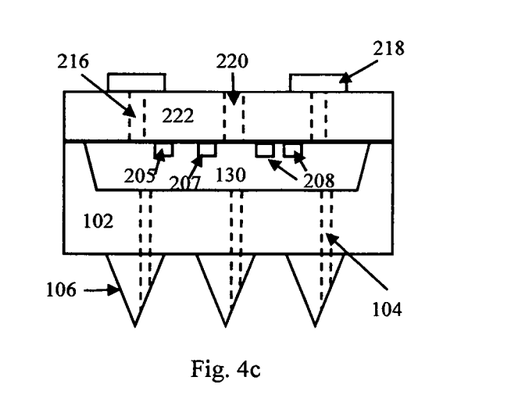

In another embodiment of the invention and as illustrated in FIGS. 4a-4c, the microfluidics chamber 130 is formed in the microneedle block 102 by chemical etching, abrasion, stamping, laser processing, or other suitable method. In the case where the microneedle block 102 is made out of silicon, the microfluidics chamber 130 can be formed by anisotropic dry etching or by wet chemical etching of the silicon which preferentially etches or stops along certain crystalline planes or by other wet or dry etching methods as is well known to those skilled in the art. An example is the case where silicon <100> wafers are used and a KOH based etchant is used to preferentially stop etching when it reaches a <111> plane forming the desired cavity. However, multiple other options based on the same concept are possible as is well known to those skilled in the art. Additionally, the venting perforation 220 is shown in block 222 for convenience but could also be easily formed laterally from the microfluidics chamber in the microneedle block 102 and be equally effective.

Figure 5:
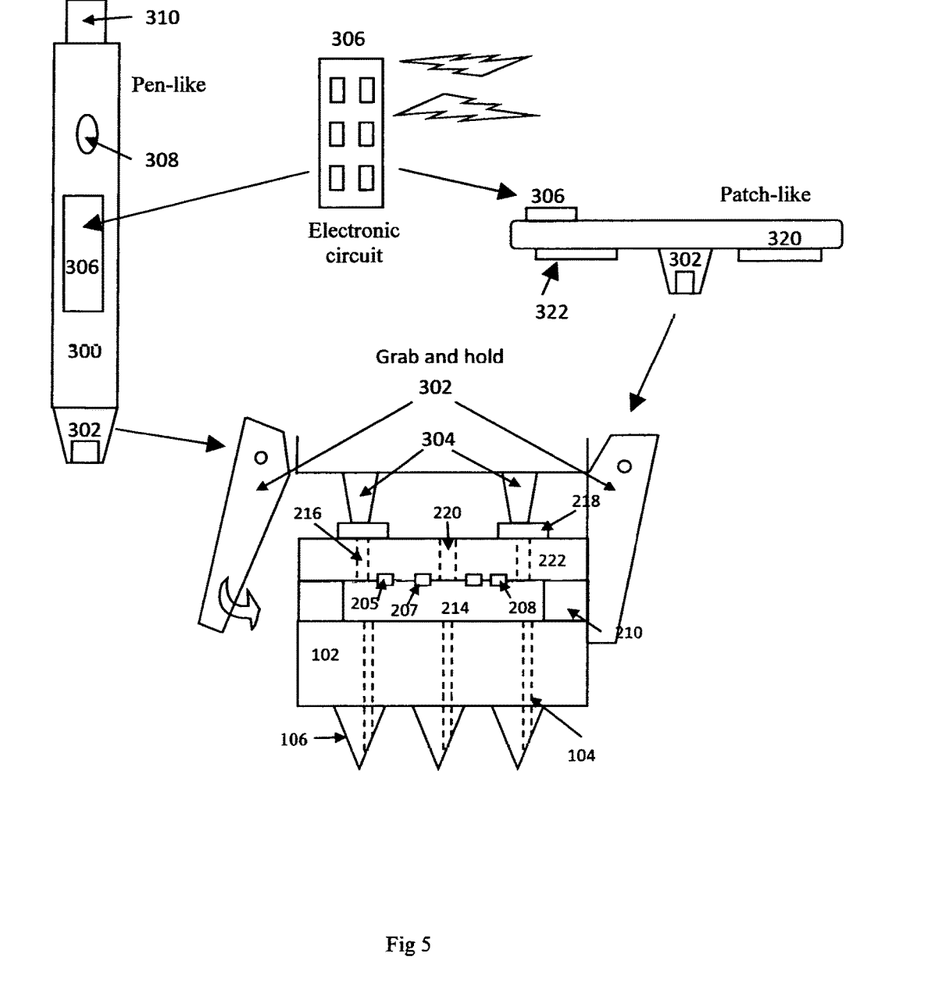
FIG. 5 represents an applicator and handling pen-like device 300, or alternatively patch-like device 320 designed to facilitate securely picking and electrically contacting the microneedle/sensor assembly and containing the power source and electronics circuit for directing and executing the sensing event and communicating the sensing results by wireless or wired connection to a smart device such as a smartphone or smart watch.

In another embodiment, as illustrated in FIG. 5, a reusable applicator 300 is designed and formed to facilitate the handling of the sensing operation in a way that is easy to use by non-specialized personnel. The applicator can be formed by using metals, ceramics, plastics, polymers, or a combination of them. As a method of illustration, the applicator 300 includes a grab-and-hold mechanism 302 that securely picks and holds the integrated sensing unit 200, means for providing electrical connectivity 304, and an electronic circuit unit 306 that provides power to the sensors by a battery or other means. The applicator has the capability to processes the results and transmit them wirelessly or by wired connection to a smart device 400. The applicator 300 also contains a mechanical grab-and-hold actuator 310, which in one embodiment of the invention could be similar to the operation of a mechanical pencil, and an electrical switch 308 that initiates the sensing sequence under user control. The description of the mechanisms, actuators and switches illustrated in FIG. 5 are provided as examples and should not be interpreted as limiting the method of executing the inventions as many related options are available to those skilled in the art. The applicator 300 itself illustrated in FIG. 5 is a pen-like device, but many other options in the form of a patch or carrier devices with alternative geometries are possible, and this example should not be construed as limiting the application of the invention. The patch-like device 320 shown in FIG. 5 illustrates such an embodiment example of the reusable applicator with its grab-and-hold mechanism 302, an adhesive 322 to secure it to the skin, and the electronics module 306 to confer a substantially similar capability and function as that described for the pen-like applicator.

Figure 6:
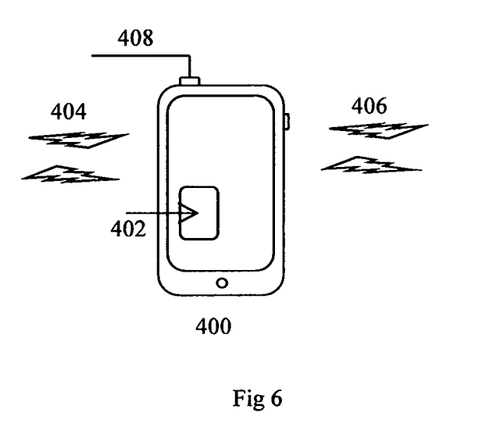
FIG. 6 represents a smart device such as a computer, a smartphone, or smart watch 400 with a specially designed application to request and direct the sensing event by communicating wireless or wired connection with the applicator device, analyze the results, communicate the results to a computer server or application in the cloud for storage and safekeeping, and communicate the results to the patient or appropriate clinician.
Figure 7:
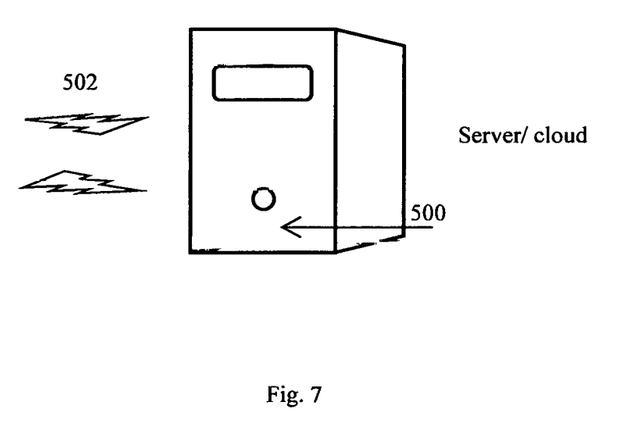
FIG. 7 represents a server computer or server in the cloud 500 with a database and a software application that receives the sensing data, performs further analysis, provides secure safekeeping of the results, and communicates the results to those with the right to know using secure protocols appropriate for medical data.
Figure 8:
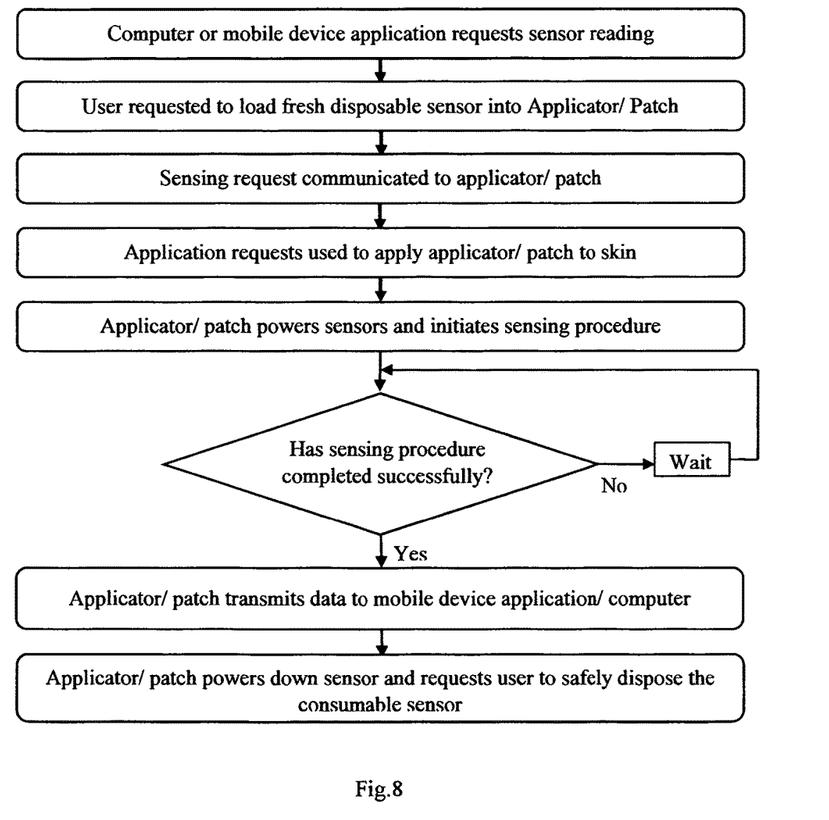
FIG. 8 represents a flow chart of the sensing event as directed by the server computer and the application in the smart device and executed by the applicator and the integrated microneedle/sensor devices.

In another embodiment as illustrated in FIG. 6, a smart device 400 such as, but not limited to a smartphone, smart watch, tablet, or computer has been equipped with a specialized application or software program that directs the sensing sequence, communicates by wire or wirelessly with the applicator 300, instructs the sensing to be done, collects and analyzes the results, and communicates them by wire or wirelessly to devices 500 under the control of the patient and/or appropriate medical personnel, as illustrated in FIG. 7. An example of the architecture of the integrated operation is described in FIG. 1 and an example of the operational flow is described in FIG. 8. It should be clear to those skilled in the art that the architecture of the integrated operation described in FIG. 1 and the operational flow described in FIG. 8 are examples and that variants in the sequence of events or modification in the flow that accomplish the same result are part of the claimed invention.

What is claimed is:

1. An apparatus for testing interstitial fluid in a subject comprising a disposable integrated micro-sensing unit and a reusable applicator,
    wherein the micro-sensing unit comprises a plurality of hollow transdermal microneedles, a microfluidics chamber, one or more sensors capable of detecting the presence or concentration of one or more analytes, a reference electrode, a pH sensor, a temperature sensor, electronic circuitry to control the testing, a casing, a spacer, a vent, and electrical contacts;
    and wherein the micro-sensing unit is configured to transmit data that result from the testing to a receiver.

2. The apparatus of claim 1 wherein the microneedles, microfluidics chamber, analyte sensors, reference electrode, pH and temperature sensors, and electronic control circuitry are formed in a monolithic block of silicon.

3. The apparatus of claim 1 wherein the microneedles are formed in a first block of silicon and the analyte sensors, reference electrode, pH and temperature sensors, and electronic control circuitry are formed in one or more additional block(s) of silicon.

4. The apparatus of claim 1 wherein the microneedles are formed in a material other than silicon.

5. The apparatus of claim 1 further comprising a substrate, wherein the substrate and microneedles are formed in a material other than silicon; the analyte sensors, reference electrode, pH and temperature sensors, and electronic control circuitry are formed in one or more additional material(s) and placed over the substrate; and the first and additional materials may be the same or different.

6. The apparatus of claim 5, wherein the analyte sensors, reference electrode, pH and temperature sensors, and electronic control circuitry are formed in material(s) other than silicon.

7. The apparatus of claim 1 wherein the microfluidics chamber is a cavity formed by the spacer, a cavity in the casing, or a cavity in a block of material comprising the microneedles.

8. The apparatus of claim 1 wherein the sensor(s) are conductivimetric, voltammetric, or amperometric.

9. The apparatus of claim 1 wherein the interior width of the hollow portion of the microneedles is less than 1 mm, the dimensions of the microfludics chamber are from 10 μm to 2 mm, the lateral dimensions of the micro-sensing unit are from 0.5 mm to 10 mm, and the thickness of the micro-sensing unit is from 0.5 mm to 5 mm.

10. The apparatus of claim 1 wherein the applicator is a pen-like or patch-like device.

11. The apparatus of claim 1 wherein the applicator comprises a battery and electronic circuitry to power the micro-sensing unit.

12. The apparatus of claim 11 wherein the applicator further comprises electronic circuitry to receive data that result from the testing and transmit the data wirelessly or by wire to a smart device or computer.

13. The apparatus of claim 12 wherein the applicator comprises a mechanical, magnetic, or electromagnetic grab-and-hold mechanism and a switch to be actuated by the user.

14. The apparatus of claim 13 wherein actuating the switch initiates the testing event when the device is ready, and wherein the execution of the testing event and transmission of the data are under full automatic control of the control circuitry without further intervention by the user.

15. The apparatus of claim 1 wherein the receiver is a computer, smart phone, smart watch, tablet computing device, or wearable computing device.

16. A method for detecting the presence or concentration of an analyte in a subject, comprising
    using the apparatus of claim 1 to apply the micro-sensing unit to the subject such that the microneedles contact interstitial fluid in the subject;
    initiating a testing event and allowing sufficient time for the interstitial fluid to reach the sensor(s);
    collecting data from the sensor(s) and transmitting the data to a receiver.

17. The method of claim 16 wherein the receiver is a computer, smart phone, smart watch, tablet computing device, or wearable computing device.

18. The method of claim 17 wherein the receiver comprises a software application capable of initiating, controlling, or directing the testing event.

19. The method of claim 17 wherein the receiver communicates the results of the testing to the user.

20. The method of claim 17 wherein the receiver further transmits the data to a server.

* * * * *